United States Patent
Takenouchi

(10) Patent No.: US 12,232,689 B2
(45) Date of Patent: Feb. 25, 2025

(54) MEDICAL IMAGE PROCESSING APPARATUS, ENDOSCOPE SYSTEM, AND MEDICAL IMAGE PROCESSING METHOD

(71) Applicant: FUJIFILM Corporation, Tokyo (JP)

(72) Inventor: Seiya Takenouchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 458 days.

(21) Appl. No.: 17/591,386

(22) Filed: Feb. 2, 2022

(65) Prior Publication Data

US 2022/0151461 A1  May 19, 2022

Related U.S. Application Data

(63) Continuation of application No. PCT/JP2020/029968, filed on Aug. 5, 2020.

(30) Foreign Application Priority Data

Aug. 13, 2019 (JP) .................................. 2019-148335

(51) Int. Cl.
    *A61B 1/00* (2006.01)
    *A61B 1/045* (2006.01)
    *G16H 30/20* (2018.01)

(52) U.S. Cl.
    CPC ...... *A61B 1/00009* (2013.01); *A61B 1/00045* (2013.01); *A61B 1/045* (2013.01); *G16H 30/20* (2018.01)

(58) Field of Classification Search
    CPC . A61B 1/00009; A61B 1/00045; A61B 1/045; A61B 1/000095; A61B 1/000096;
    (Continued)

(56) References Cited

U.S. PATENT DOCUMENTS

2016/0165222 A1  6/2016  Yamaoka et al.
2020/0058124 A1* 2/2020  Iwaki ..................... G06T 7/0012
(Continued)

FOREIGN PATENT DOCUMENTS

JP   2006-129950 A   5/2006
JP   2015-112429 A   6/2015
(Continued)

OTHER PUBLICATIONS

An Office Action; "Notice of Reasons for Refusal," mailed by the Japanese Patent Office on Sep. 1, 2022, which corresponds to Japanese Patent Application No. 2021-539231 and is related to U.S. Appl. No. 17/591,386; with English language translation.
(Continued)

*Primary Examiner* — Md K Talukder
(74) *Attorney, Agent, or Firm* — Studebaker & Brackett PC

(57) ABSTRACT

An object of the present invention is to provide a medical image processing apparatus, an endoscope system, and a medical image processing method that are capable of causing a user to appropriately recognize an operation state of an assistance function. A medical image processing apparatus according to a first aspect of the present invention includes an image acquiring unit that acquires a chronological medical image; a recognizing unit that performs recognition of a region of interest in the acquired medical image; a reporting unit that performs reporting of a result of the recognition in at least one style and that, in response to a predetermined condition being satisfied after start of a reporting state of performing the reporting, is switched to a non-reporting state of not performing the reporting; and a switching notifying unit that provides a notification indicating that switching from the reporting state to the non-reporting state is to occur.

23 Claims, 11 Drawing Sheets

(58) Field of Classification Search
CPC ... A61B 1/043; A61B 1/0638; A61B 1/00055; A61B 1/000094; G16H 30/20; G16H 15/00; G16H 30/40; G16H 40/67; G16H 50/20
See application file for complete search history.

(56) References Cited

U.S. PATENT DOCUMENTS

| | | | |
|---|---|---|---|
| 2020/0069160 A1 | 3/2020 | Oosake | |
| 2020/0242766 A1 | 7/2020 | Endo | |
| 2020/0297422 A1* | 9/2020 | Gocho | A61B 1/00055 |
| 2022/0151461 A1* | 5/2022 | Takenouchi | A61B 1/00009 |
| 2022/0313067 A1* | 10/2022 | Meguro | A61B 1/00045 |
| 2022/0383533 A1* | 12/2022 | Takenouchi | A61B 1/0005 |

FOREIGN PATENT DOCUMENTS

| | | |
|---|---|---|
| JP | 2016-111533 A | 6/2016 |
| WO | 2018/198161 A1 | 11/2018 |
| WO | 2018/221033 A1 | 12/2018 |
| WO | 2019/078102 A1 | 4/2019 |
| WO | 2019/082993 A1 | 5/2019 |
| WO | WO-2019116592 A1 * | 6/2019 ......... A61B 1/00006 |

OTHER PUBLICATIONS

International Search Report issued in PCT/JP2020/029968; mailed Oct. 20, 2020.

International Preliminary Report on Patentability and Written Opinion issued in PCT/JP2020/029968; issued Feb. 8, 2022.

An Office Action; "Notice of Reasons for Refusal," mailed by the Japanese Patent Office on Jan. 19, 2023, which corresponds to Japanese Patent Application No. 2021-539231 and is related to U.S. Appl. No. 17/591,386; with English language translation.

* cited by examiner

MEDICAL IMAGE PROCESSING APPARATUS, ENDOSCOPE SYSTEM, AND MEDICAL IMAGE PROCESSING METHOD

CROSS-REFERENCE TO RELATED APPLICATIONS

The present application is a Continuation of PCT International Application No. PCT/JP2020/029968 filed on Aug. 5, 2020 claiming priority under 35 U.S.C. § 119(a) to Japanese Patent Application No. 2019-148335 filed on Aug. 13, 2019. Each of the above applications is hereby expressly incorporated by reference, in its entirety, into the present application.

BACKGROUND OF THE INVENTION

1. Field of the Invention

The present invention relates to a medical image processing apparatus, an endoscope system, and a medical image processing method that report a recognition result of a medical image.

2. Description of the Related Art

In various types of medical image processing apparatuses, a technique of assisting a user in efficiently performing an examination or diagnosis is expected. For example, it may be possible to report a candidate lesion region, cancerousness of a lesion, or an invasive depth of a lesion in an observation image to a user. For example, JP2006-129950A describes a capsule endoscope that outputs a notification sound (pre-warning sound, report sound, termination sound) providing a notification indicating that a feature image is to be displayed.

SUMMARY OF THE INVENTION

Assistance using various types of reporting is useful to a user, but excessive assistance may not only interfere with concentration of the user but also disturb an examination. Thus, it is preferable to end assistance as appropriate. On the other hand, user's attention is directed toward operating a device or observing a result during an examination, and thus an operation state of an assistance function may be unrecognizable by the user. However, the existing technique as described in JP2006-129950A mentioned above does not sufficiently take these points into consideration.

The present invention has been made in view of these circumstances, and it is an object of the present invention to provide a medical image processing apparatus, an endoscope system, and a medical image processing method that are capable of causing a user to sufficiently recognize an operation state of an assistance function.

To achieve the above-described object, a medical image processing apparatus according to a first aspect of the present invention includes an image acquiring unit that acquires a chronological medical image; a recognizing unit that performs recognition of a region of interest in the acquired medical image; a reporting unit that performs reporting of a result of the recognition in at least one style and that, in response to a predetermined condition being satisfied after start of a reporting state of performing the reporting, is switched to a non-reporting state of not performing the reporting; and a switching notifying unit that provides a notification indicating that switching from the reporting state to the non-reporting state is to occur. The medical image processing apparatus according to the first aspect includes the reporting unit that performs reporting of a result of the recognition in at least one style and that, in response to a predetermined condition being satisfied after start of a reporting state of performing the reporting, is switched to a non-reporting state of not performing the reporting, and is thus capable of ending assistance as appropriate (in accordance with the predetermined condition). In addition, the medical image processing apparatus includes the switching notifying unit that provides a notification indicating that switching from the reporting state to the non-reporting state is to occur, and is thus capable of causing a user to sufficiently recognize an operation state of an assistance function (switching from the reporting state to the non-reporting state).

In the first aspect, the "predetermined condition" can be set regarding an elapsed time of the reporting state or the non-reporting state, whether a user operation has been performed or content of the user operation, a recognition result of a region of interest, or the like. The medical image processing apparatus may set the condition in accordance with a user operation or regardless of a user operation.

In the first aspect, the "region of interest" may include a legion region, a candidate lesion region, or a region that has been treated, and the "recognition" of the region of interest may include determination (detection, measurement, classification, or the like) of the presence, number, position, size, shape, type, or motion in an image of the region of interest, the level of lesion, or the like. The "acquisition of a medical image" includes sequentially acquiring a plurality of medicate images captured at a determined frame rate. The acquisition may or may not be performed in real time. The image acquiring unit may acquire a plurality of medical images by capturing images using an imaging apparatus including an imaging optical system and an imaging element, or may acquire a plurality of medical images recorded in advance via a network and/or a recording medium.

The medical image processing apparatus according to the first aspect can be implemented as, for example, a processor of a medical image processing system, but is not limited to such an aspect. The "medical image" is an image acquired as a result of imaging, measurement, or the like performed on a living body, such as a human body, for the purpose of diagnosis, treatment, measurement, or the like, and may be, for example, an endoscopic image, an ultrasound image, a computed tomography (CT) image, or a magnetic resonance imaging (MRI) image.

In a medical image processing apparatus according to a second aspect, in the first aspect, the switching notifying unit provides a notification indicating that a state of the reporting is to be switched from the non-reporting state to the reporting state. According to the second aspect, it is possible to cause a user to sufficiently recognize switching from the non-reporting state to the reporting state.

In a medical image processing apparatus according to a third aspect, in the second aspect, the switching notifying unit provides a notification of switching from the reporting state to the non-reporting state in a first style, and provides a notification of switching from the non-reporting state to the reporting state in a second style different from the first style. According to the third aspect, the style of switching from the reporting state to the non-reporting state is different from the style of switching from the non-reporting state to the reporting state, and thus a user is capable of clearly grasping switching of the state of reporting.

In a medical image processing apparatus according to a fourth aspect, in any one of the first to third aspects, the reporting unit is switched to the non-reporting state after a determined time has elapsed from start of the reporting state, and the switching notifying unit provides a notification of switching from the reporting state to the non-reporting state. According to the fourth aspect, excessive notification can be suppressed.

In a medical image processing apparatus according to a fifth aspect, in any one of the first to fourth aspects, the reporting unit is switched from the non-reporting state to the reporting state after a determined time has elapsed from when the recognizing unit recognizes the region of interest, and the switching notifying unit provides a notification of switching to the reporting state. According to the fifth aspect, a decrease in attention to a medical image can be suppressed, and impediment to an increase in capability of finding a region of interest can be removed.

In a medical image processing apparatus according to a sixth aspect, in any one of the first to fifth aspects, the switching notifying unit provides the notification a determined time before switching of a state of the reporting. According to the sixth aspect, a user is capable of grasping switching of the state of reporting in advance.

In a medical image processing apparatus according to a seventh aspect, in any one of the first to fifth aspects, the switching notifying unit provides the notification at the same time as switching of a state of the reporting. According to the seventh aspect, a user is capable of grasping switching of the state of reporting.

In a medical image processing apparatus according to an eighth aspect, in any one of the first to seventh aspects, the switching notifying unit provides the notification by using at least one of an audio signal, a light signal, an image signal, or a vibration signal. The eighth aspect defines a specific aspect of the signal used for notification.

In a medical image processing apparatus according to a ninth aspect, in any one of the first to eighth aspects, the switching notifying unit provides the notification in a style different from a style of the reporting. In the ninth aspect, the switching notifying unit performs "notification" of providing a notification of switching of the state of reporting in a style different from a style of "reporting" of reporting that the recognizing unit has recognized a region of interest, and thus a user is capable of easily grasping which of "reporting" and "notification" is being performed.

In a medical image processing apparatus according to a tenth aspect, in any one of the first to ninth aspects, the medical image processing apparatus further includes a setting unit that sets a style of the reporting and/or the notification. The setting unit is capable of setting a style of reporting and/or notification in accordance with a user operation.

In a medical image processing apparatus according to an eleventh aspect, in any one of the first to tenth aspects, the recognizing unit recognizes the region of interest without image processing on the medical image. The recognizing unit is capable of recognizing a region of interest by, for example, audio input, image recognition of a gesture of a user, or an operation of a device such as a foot switch.

To achieve the above-described object, an endoscope system according to a twelfth aspect of the present invention includes the medical image processing apparatus according to any one of the first to eleventh aspects, a display apparatus that displays the medical image, and an endoscope that is to be inserted into a subject and that has an imaging unit that captures the medical image. The endoscope system according to the twelfth aspect includes the medical image processing apparatus according to any one of the first to eleventh aspects, and is thus capable of causing a user to sufficiently recognize an operation state of an assistance function.

To achieve the above-described object, a medical image processing method according to a thirteenth aspect of the present invention includes an image acquisition step of acquiring a chronological medical image; a recognition step of performing recognition of a region of interest in the acquired medical image; a reporting step of performing reporting of a result of the recognition in at least one style and of, in response to a predetermined condition being satisfied after start of a reporting state of performing the reporting, performing switching to a non-reporting state of not performing the reporting; and a switching notification step of providing a notification indicating that switching from the reporting state to the non-reporting state is to occur. According to the thirteenth aspect, as in the first aspect, it is possible to cause a user to sufficiently recognize an operation state of an assistance function. The medical image processing method according to the thirteenth aspect may further include configurations similar to those according to the second to eleventh aspects. In addition, a program that causes the medical image processing apparatus or a computer to execute the medical image processing method according to these aspects, and a non-transitory recording medium storing computer-readable code of the program are also included in an aspect of the present invention.

As described above, the medical image processing apparatus, the endoscope system, and the medical image processing method according to the present invention are capable of causing a user to sufficiently recognize an operation state of an assistance function.

DESCRIPTION OF THE PREFERRED EMBODIMENTS

Hereinafter, an embodiment of a medical image processing apparatus, an endoscope system, and a medical image processing method according to the present invention will be described in detail with reference to the accompanying drawings.

First Embodiment

Configuration of Endoscope System

Figure 1:
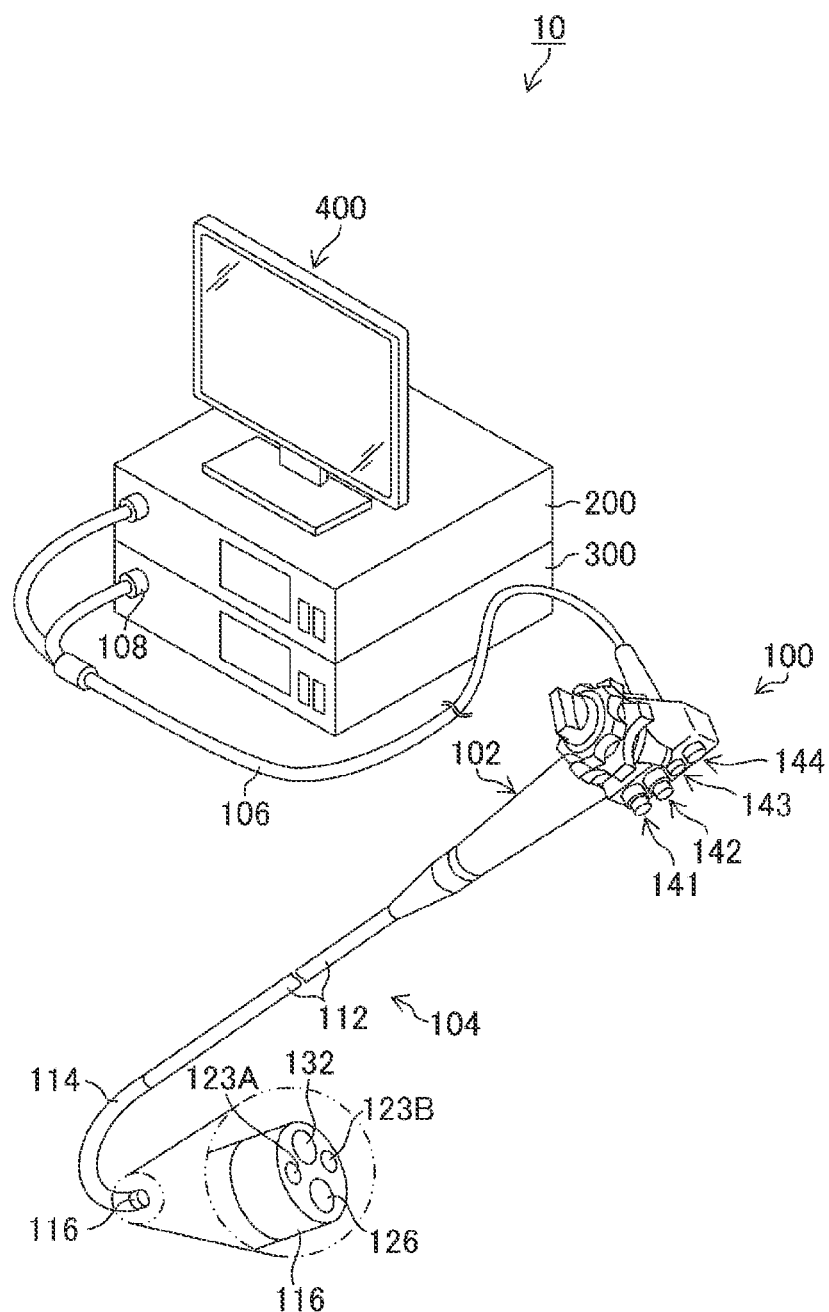
FIG. 1 is a diagram illustrating the configuration of an endoscope system according to a first embodiment.
Figure 2:
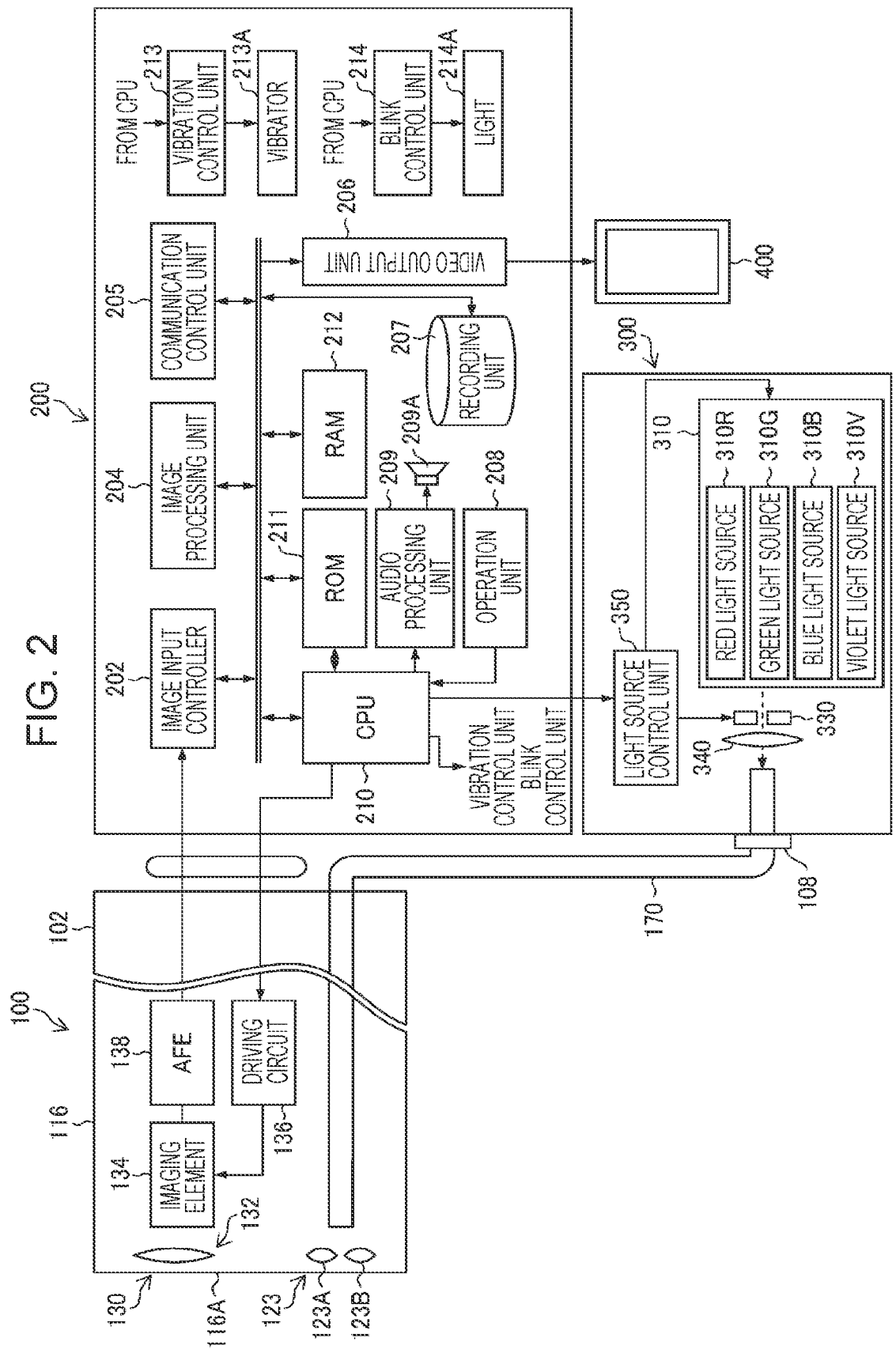
FIG. 2 is another diagram illustrating the configuration of the endoscope system.

FIG. 1 is an external appearance diagram of an endoscope system 10 (a medical image processing apparatus, an endoscope system), and FIG. 2 is a block diagram illustrating the configuration of a main part of the endoscope system 10. As illustrated in FIGS. 1 and 2, the endoscope system 10 is constituted by an endoscope 100 (a medical apparatus, an endoscope, an endoscope main body), a processor 200 (a medical image processing apparatus), a light source apparatus 300 (a light source apparatus), and a monitor 400 (a display apparatus). An external device (not illustrated) for acquiring area information by using an electromagnetic wave or an ultrasonic wave may be connected to the endoscope system 10.

Configuration of Endoscope

The endoscope 100 includes a handheld operation section 102 and an insertion section 104 that communicates with the handheld operation section 102. An operator (a user) operates the handheld operation section 102 while grasping it and inserts the insertion section 104 into a body of a subject (a living body) to perform observation. The handheld operation section 102 is provided with an air/water supply button 141, a suction button 142, a function button 143 to which various functions are allocated, and an imaging button 144 for receiving an imaging instruction operation (a still image, a moving image). The insertion section 104 is constituted by a soft part 112, a bending part 114, and a tip rigid part 116, which are arranged in this order from the handheld operation section 102 side. That is, the bending part 114 is connected to a base end side of the tip rigid part 116, and the soft part 112 is connected to a base end side of the bending part 114. The handheld operation section 102 is connected to a base end side of the insertion section 104. The user is able to change the orientation of the tip rigid part 116 in an up, down, left, or right direction by causing the bending part 114 to bend by operating the handheld operation section 102. The tip rigid part 116 is provided with an imaging optical system 130, an illumination unit 123, a forceps port 126, and so forth (see FIGS. 1 and 2).

During observation or treatment, an operation of an operation unit 208 (see FIG. 2) enables white light and/or narrow-band light (one or more of red narrow-band light, green narrow-band light, blue narrow-band light, and violet narrow-band light) to be radiated from illumination lenses 123A and 123B of the illumination unit 123. In addition, an operation of the air/water supply button 141 enables washing water to be ejected from a water supply nozzle that is not illustrated, so that an imaging lens 132 (an imaging lens, an imaging unit) of the imaging optical system 130 and the illumination lenses 123A and 123B can be washed. The forceps port 126 opening in the tip rigid part 116 communicates with a pipe line that is not illustrated, so that a treatment tool that is not illustrated and is for extirpating a tumor or the like can be inserted into the pipe line and necessary treatment can be given to a subject by moving the treatment tool forward or backward as appropriate.

As illustrated in FIGS. 1 and 2, the imaging lens 132 (an imaging unit) is disposed on a distal-end-side surface 116A of the tip rigid part 116. A complementary metal-oxide semiconductor (CMOS) imaging element 134 (an imaging element, an imaging unit), a driving circuit 136, and an analog front end (AFE) 138 (an imaging unit) are disposed behind the imaging lens 132, and these elements output an image signal. The imaging element 134 is a color imaging element and includes a plurality of pixels constituted by a plurality of light-receiving elements arranged in a matrix (arranged two-dimensionally) in a specific pattern arrangement (Bayer arrangement, X-Trans (registered trademark) arrangement, honeycomb arrangement, or the like). Each pixel of the imaging element 134 includes a microlens, a red (R), green (G), or blue (B) color filter, and a photoelectric conversion unit (a photodiode or the like). The imaging optical system 130 is capable of generating a color image from pixel signals of three colors, red, green, and blue, and is also capable of generating an image from pixel signals of any one or two colors among red, green, and blue. In the first embodiment, a description will be given of a case where the imaging element 134 is a CMOS imaging element, but the imaging element 134 may be a charge coupled device (CCD) imaging element. Each pixel of the imaging element 134 may further include a violet color filter corresponding to a violet light source 310V and/or an infrared filter corresponding to an infrared light source.

An optical image of a subject is formed on a light-receiving surface (an imaging surface) of the imaging element 134 by the imaging lens 132, converted into an electric signal, output to the processor 200 through a signal cable that is not illustrated, and converted into a video signal. Accordingly, an endoscopic image is displayed on the monitor 400, which is connected to the processor 200.

The illumination lenses 123A and 123B of the illumination unit 123 are provided next to the imaging lens 132 on the distal-end-side surface 116A of the tip rigid part 116. An emission end of a light guide 170, which will be described below, is disposed behind the illumination lenses 123A and 123B. The light guide 170 extends through the insertion section 104, the handheld operation section 102, and a universal cable 106, and an incidence end of the light guide 170 is located in a light guide connector 108.

A user performs imaging (under control of the imaging unit and an image acquiring unit 220) at a determined frame rate while inserting or removing the endoscope 100 (the insertion section 104) having the above-described configuration into or from a living body as a subject, thereby being capable of sequentially capturing images of the inside of the living body.

Configuration of Light Source Apparatus

As illustrated in FIG. 2, the light source apparatus 300 is constituted by a light source 310 for illumination, a diaphragm 330, a condenser lens 340, a light source control unit 350, and so forth, and causes observation light to enter the light guide 170. The light source 310 includes a red light source 310R, a green light source 310G, a blue light source 310B, and the violet light source 310V that radiate red narrow-band light, green narrow-band light, blue narrow-band light, and violet narrow-band light, respectively, and is capable of radiating red narrow-band light, green narrow-band light, blue narrow-band light, and violet narrow-band light. The illuminance of observation light from the light source 310 is controlled by the light source control unit 350, which is capable of changing (increasing or decreasing) the illuminance of observation light or stopping illumination as necessary.

The light source 310 is capable of emitting red narrow-band light, green narrow-band light, blue narrow-band light, and violet narrow-band light in any combination. For example, the light source 310 is capable of simultaneously emitting red narrow-band light, green narrow-band light, blue narrow-band light, and violet narrow-band light to radiate white light (normal light) as observation light, and is also capable of emitting any one or two of red narrow-band light, green narrow-band light, blue narrow-band light, and violet narrow-band light to radiate narrow-band light (special light). The light source 310 may further include an infrared light source that radiates infrared light (an example of narrow-band light). Alternatively, with use of a light source that radiates white light and a filter that allows white light and each narrow-band light to pass therethrough, white light or narrow-band light may be radiated as observation light.

Wavelength Range of Light Source

The light source 310 may be a light source that generates light in a white range or light in a plurality of wavelength ranges as the light in the white range, or may be a light source that generates light in a specific wavelength range narrower than the white wavelength range. The specific wavelength range may be a blue range or green range in a visible range, or may be a red range in the visible range. In a case where the specific wavelength range is the blue range or green range in the visible range, the specific wavelength range may include a wavelength range of 390 nm or more and 450 nm or less or a wavelength range of 530 nm or more and 550 nm or less, and the light in the specific wavelength range may have a peak wavelength in the wavelength range of 390 nm or more and 450 nm or less or the wavelength range of 530 nm or more and 550 nm or less. In a case where the specific wavelength range is the red range in the visible range, the specific wavelength range may include a wavelength range of 585 nm or more and 615 nm or less or a wavelength range of 610 nm or more and 730 nm or less, and the light in the specific wavelength range may have a peak wavelength in the wavelength range of 585 nm or more and 615 nm or less or the wavelength range of 610 nm or more and 730 nm or less.

The above-described specific wavelength range may include a wavelength range in which a light absorption coefficient is different between oxyhemoglobin and deoxyhemoglobin, and the light in the specific wavelength range may have a peak wavelength in the wavelength range in which the light absorption coefficient is different between oxyhemoglobin and deoxyhemoglobin. In this case, the specific wavelength range may include a wavelength range of 400±10 nm, a wavelength range of 440±10 nm, a wavelength range of 470±10 nm, or a wavelength range of 600 nm or more and 750 nm or less, and the light in the specific wavelength range may have a peak wavelength in the wavelength range of 400±10 nm, the wavelength range of 440±10 nm, the wavelength range of 470±10 nm, or the wavelength range of 600 nm or more and 750 nm or less.

The wavelength range of the light generated by the light source 310 may include a wavelength range of 790 nm or more and 820 nm or less or a wavelength range of 905 nm or more and 970 nm or less, and the light generated by the light source 310 may have a peak wavelength in the wavelength range of 790 nm or more and 820 nm or less or the wavelength range of 905 nm or more and 970 nm or less.

Alternatively, the light source 310 may include a light source that radiates excitation light whose peak is 390 nm or more and 470 nm or less. In this case, a medical image (an inside-of-living-body image) having information about fluorescence emitted by a fluorescent substance in a subject (a living body) can be acquired. In the case of acquiring a fluorescence image, a pigment for a fluorescence method (fluorescein, acridine orange, or the like) may be used.

It is preferable that the type of the light source 310 (a laser light source, a xenon light source, a light-emitting diode (LED) light source, or the like), the wavelength of the light source 310, the presence or absence of a filter for the light source 310, and so forth be determined in accordance with the type of photographic subject, an area of the photographic subject, the purpose of observation, or the like. It is also preferable that, during observation, the wavelengths of observation light be combined and/or switched in accordance with the type of photographic subject, an area of the photographic subject, the purpose of observation, or the like. In the case of switching the wavelength, for example, a disc-shaped filter (a rotary color filter) that is disposed in front of the light source and that is provided with a filter for transmitting or blocking light of a specific wavelength may be rotated to switch the wavelength of light to be radiated.

The imaging element used to carry out the present invention is not limited to a color imaging element in which color filters are disposed for the individual pixels, such as the imaging element 134, and may be a monochrome imaging element. In the case of using a monochrome imaging element, imaging can be performed in a frame sequential (color sequential) manner by sequentially switching the wavelength of observation light. For example, the wavelength of outgoing observation light may be sequentially switched among violet, blue, green, and red, or wide-band light (white light) may be radiated and the wavelength of outgoing observation light may be switched by using a rotary color filter (red, green, blue, violet, and the like). Alternatively, one or a plurality of types of narrow-band light (green, blue, violet, and the like) may be radiated and the wavelength of outgoing observation light may be switched by using a rotary color filter (green, blue, violet, and the like). The narrow-band light may be infrared light of two or more different wavelengths (first narrow-band light and second narrow-band light).

As a result of connecting the light guide connector 108 (see FIGS. 1 and 2) to the light source apparatus 300, observation light radiated by the light source apparatus 300 is transmitted through the light guide 170 to the illumination lenses 123A and 123B and is radiated from the illumination lenses 123A and 123B to an observation range.

Configuration of Processor

The configuration of the processor 200 will be described with reference to FIG. 2. In the processor 200, an image input controller 202 receives an image signal output from the endoscope 100, an image processing unit 204 performs necessary image processing thereon, and a video output unit 206 outputs a resulting image signal. Accordingly, an observation image (an inside-of-living-body image) is displayed on the monitor 400 (a display apparatus). These processing operations are performed under control by a central processing unit (CPU) 210. A communication control unit 205 controls communication, for a medical image or area information, with a hospital information system (HIS), a hospital local area network (LAN), and/or an external system or network that are not illustrated. In a recording unit 207 (a recording apparatus), an image of a subject (an endoscopic image, a medical image), information indicating a result of recognition (detection, classification, measurement, etc.), and the like are recorded (see FIG. 6 and the description related thereto). An audio processing unit 209 (a reporting unit, a switching notifying unit) outputs a message (an audio signal) about recognition, reporting, or notification of a region of interest from a speaker 209A under control by the CPU 210 and the image processing unit 204. A vibration control unit 213 (a reporting unit, a switching notifying unit)

causes a vibrator 213A to vibrate to perform reporting or notification (output a vibration signal) under control by the CPU 210 and the image processing unit 204. A blink control unit 214 (a reporting unit, a switching notifying unit) causes a light 214A to be turned on or off to perform reporting or notification (output a light signal) under control by the CPU 210 and the image processing unit 204.

A read only memory (ROM) 211 is a nonvolatile storage element (a non-transitory recording medium) and stores a computer-readable code of a program that causes the CPU 210 and/or the image processing unit 204 (a medical image processing apparatus, a computer) to execute various image processing methods. A random access memory (RAM) 212 is a storage element for temporary storage in various processing operations and can be used as a buffer at the time of acquiring an image.

A user is capable of providing an instruction to execute medical image processing or designating a condition necessary for the execution via the operation unit 208. A setting unit 228, a reporting unit 224, and a switching notifying unit 226 are capable of causing the monitor 400 to display a screen of these instructions, a result of recognition, and so forth.

Functions of Image Processing Unit

Figure 3:
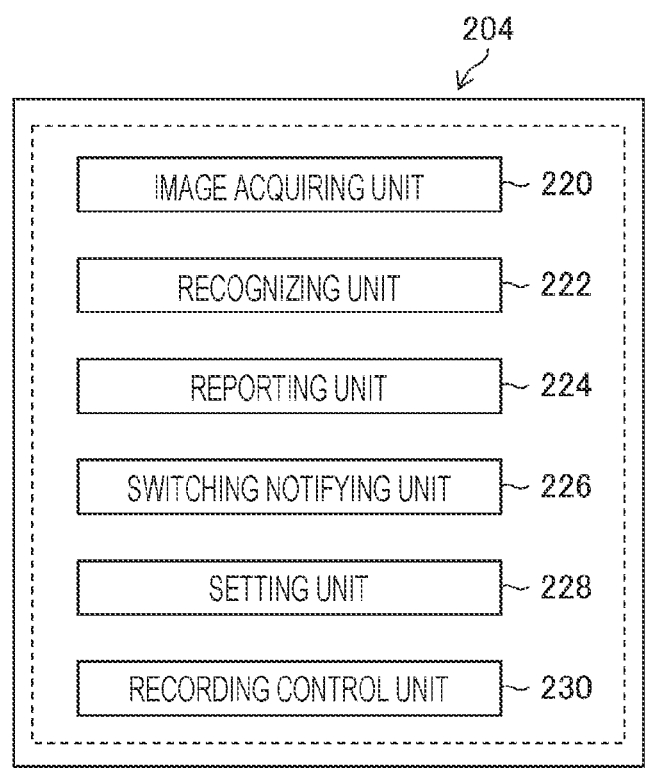
FIG. 3 is a functional block diagram of an image processing unit.

FIG. 3 is a functional block diagram of the image processing unit 204. The image processing unit 204 includes the image acquiring unit 220 (an image acquiring unit), a recognizing unit 222 (a recognizing unit), the reporting unit 224 (a reporting unit), the switching notifying unit 226 (a switching notifying unit), the setting unit 228 (a setting unit), and a recording control unit 230 (a recoding control unit). Medical image processing using these functions will be described in detail below.

The image processing unit 204 is capable of performing, with the above-described functions, calculation of a feature quantity of a medical image, processing of emphasizing or reducing a component of a specific frequency band, and processing of emphasizing or deemphasizing a specific target (a region of interest, blood vessels at a desired depth, or the like). The image processing unit 204 may include a special-light image acquiring unit that acquires a special-light image having information about a specific wavelength range on the basis of a normal-light image that is acquired by radiating light in the white range or light in a plurality of wavelength ranges as the light in the white range. In this case, a signal in the specific wavelength range can be acquired through computation based on color information of RGB (R: red, G: green, B: blue) or CMY (C: cyan, M: magenta, Y: yellow) included in the normal-light image. In addition, the image processing unit 204 may include a feature quantity image generating unit that generates a feature quantity image through computation based on at least one of a normal-light image that is acquired by radiating light in the white range or light in a plurality of wavelength ranges as the light in the white range or a special-light image that is acquired by radiating light in a specific wavelength range, and may acquire and display the feature quantity image as a medical image. The above-described processing is performed under control by the CPU 210.

Implementation of Functions by Various Processors

The above-described functions of the individual units of the image processing unit 204 can be implemented by using various types of processors and a recording medium. The various types of processors include, for example, a central processing unit (CPU) which is a general-purpose processor that executes software (program) to implement various functions. Also, the various types of processors include a graphics processing unit (GPU) which is a processor dedicated to image processing, and a programmable logic device (PLD) which is a processor whose circuit configuration is changeable after manufacturing, such as a field programmable gate array (FPGA). In the case of performing learning and recognition of images as in the present invention, the configuration using a GPU is effective. Furthermore, the various types of processors include a dedicated electric circuit which is a processor having a circuit configuration designed exclusively for executing specific processing, such as an application specific integrated circuit (ASIC).

The function of each unit may be implemented by one processor or may be implemented by a plurality of processors of the same type or different types (for example, a combination of a plurality of FPGAs, a combination of a CPU and an FPGA, or a combination of a CPU and a GPU). A plurality of functions may be implemented by one processor. A first example of implementing a plurality of functions by one processor is that a combination of one or more CPUs and software constitutes one processor and the one processor implements the plurality of functions, as represented by a computer. A second example is that a processor that implements the functions of an entire system by one integrated circuit (IC) chip is used, as represented by a system on chip (SoC). In this way, various functions are configured as a hardware structure by using one or more of the above-described various types of processors. Furthermore, the hardware structure of the various types of processors is, more specifically, electric circuitry formed by combining circuit elements such as semiconductor elements. The electric circuitry may be electric circuitry that implements the above-described functions by using logical disjunction, logical conjunction, logical negation, exclusive disjunction, and logical operation as a combination thereof.

When the above-described processor or electric circuitry executes the software (program), the code of the software to be executed that is readable by a computer (for example, the various types of processors or electric circuitry constituting the image processing unit 204, and/or a combination thereof) is stored in a non-transitory recording medium, such as the read only memory (ROM) 211, and the computer refers to the software. The software stored in the non-transitory recording medium includes a program for executing the medical image processing method according to the present invention and data to be used for the execution (data used to specify an image processing condition, a reporting style, or a notification style). The code may be recorded on a non-transitory recording medium, such as a magneto-optical recording device of various types or a semiconductor memory, instead of the ROM 211. In the processing using the software, the random access memory (RAM) 212 may be used as a transitory storage region, for example, and data stored in an electrically erasable and programmable read only memory (EEPROM) that is not illustrated can be referred to, for example. The recording unit 207 may be used as a "non-transitory recording medium".

Recognizing Unit Using Learned Model

The above-described recognizing unit 222 (a recognizing unit: a detector, a classifier, a measurer) can be constituted by using a learned model (a model learned by using an image set constituted by captured images of a living body), such as a convolutional neural network (CNN) or a support vector machine (SVM). Hereinafter, a description will be given of a layer configuration in a case where the recognizing unit 222 is constituted by a CNN. The description will be given mainly of a case where the recognizing unit 222 is a detector (for detecting a region of interest). However, a similar layer configuration can be adopted for classification (discrimination) or measurement.

Examples of Layer Configuration of CNN

Figure 4A:
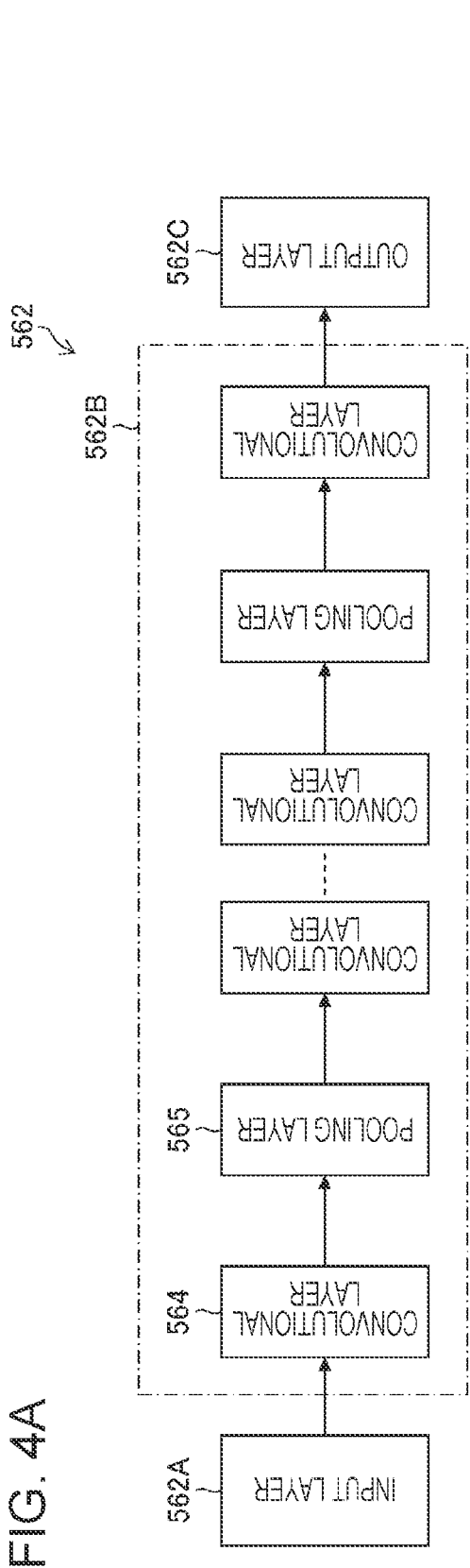
FIGS. 4A and 4B are diagrams illustrating configuration examples of a convolutional neural network.
Figure 4B:
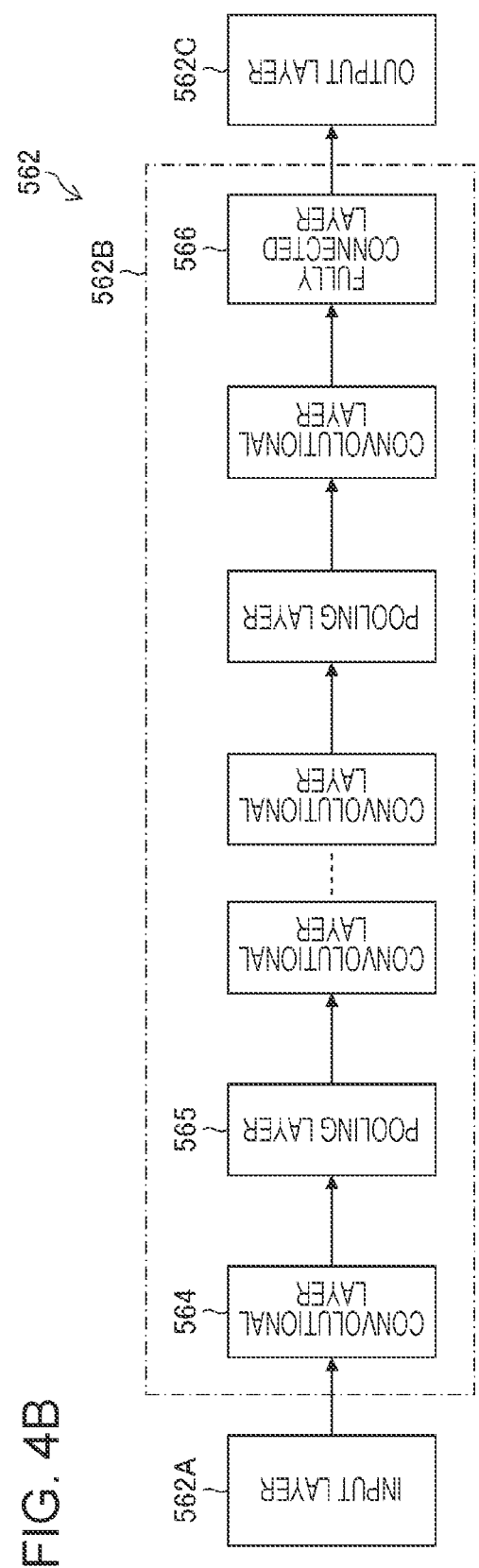

FIGS. 4A and 4B are diagrams illustrating examples of the layer configuration of a CNN. In the example illustrated in FIG. 4A, a CNN 562 includes an input layer 562A, an intermediate layer 562B, and an output layer 562C. The input layer 562A receives an endoscopic image (medical image) acquired by the image acquiring unit 220 and outputs a feature quantity. The intermediate layer 562B includes convolutional layers 564 and pooling layers 565, and receives the feature quantity output from the input layer 562A and calculates another feature quantity. These layers each have a structure in which a plurality of "nodes" are connected by "edges" and hold a plurality of weight parameters. The values of the weight parameters change as learning progresses. The CNN 562 may include a fully connected layer 566 as in the example illustrated in FIG. 4B. The layer configuration of the CNN 562 is not limited to the configuration in which the convolutional layers 564 and the pooling layers 565 are alternately arranged, and may include a plurality of consecutive convolutional layers 564 or pooling layers 565 (for example, convolutional layers 564). Alternatively, a plurality of consecutive fully connected layers 566 may be included.

Processing in Intermediate Layer

The intermediate layer 562B calculates a feature quantity through convolutional operation and pooling processing. The convolutional operation performed in the convolutional layer 564 is processing of acquiring a feature map through convolutional operation using a filter, and plays a role in feature extraction such as edge extraction from an image. As a result of the convolutional operation using a filter, one-channel (one) "feature map" is created for one filter. The size of the "feature map" is scaled down by convolution and is reduced as convolution is performed in each layer. The pooling processing performed in the pooling layer 565 is processing of reducing (or enlarging) the feature map output through the convolutional operation to create a new feature map, and plays a role in giving robustness so that the extracted feature is not affected by parallel movement or the like. The intermediate layer 562B can be constituted by one or a plurality of layers that perform these processing operations.

Figure 5:
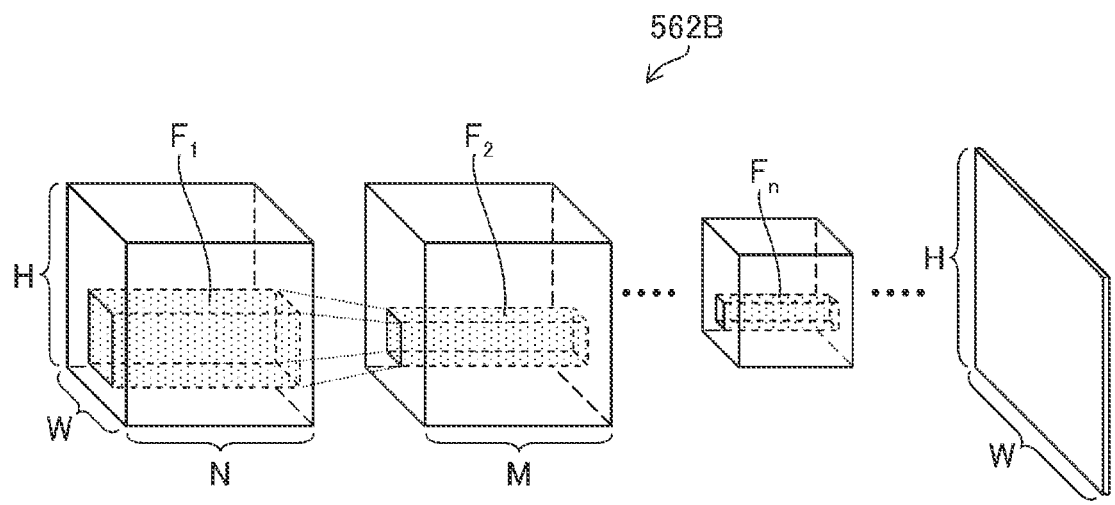
FIG. 5 is a diagram illustrating a state of convolutional processing using filters.

FIG. 5 is a schematic diagram illustrating an example configuration of the intermediate layer 562B of the CNN 562 illustrated in FIGS. 4A and 4B. In the first convolutional layer of the intermediate layer 562B, convolutional operation of an image set constituted by a plurality of medical images (a learning image set in the case of learning, and a recognition image set in the case of recognition) and a filter $F_1$ is performed. The image set is constituted by N (N-channel) images each having an image size in which the height is represented by H and the width is represented by W. In the case of inputting normal-light images, the images constituting an image set are three-channel images of red (R), green (G), and blue (B). The filter $F_1$ convoluted with this image set has a filter size of 5×5×N in the case of the filter having size 5 (5×5), for example, because the image set has N channels (N images). As a result of convolutional operation using the filter $F_1$, one-channel (one) "feature map" is created for one filter $F_1$. A filter $F_2$ used in the second convolutional layer has a filter size of 3×3×M in the case of the filter having size 3 (3×3), for example.

As in the first convolutional layer, in the second to n-th convolutional layers, convolutional operations using filters $F_2$ to $F_n$ are performed, respectively. The size of the "feature map" in the n-th convolutional layer is smaller than the size of the "feature map" in the second convolutional layer because scaling-down is performed in the convolutional layers or pooling layers in the preceding stages.

In the layers of the intermediate layer 562B, lower-order feature extraction (extraction of edges or the like) is performed in a convolutional layer near the input side, and higher-order feature extraction (extraction of features about the shape, structure, and the like of an object) is performed near the output side. In the case of performing segmentation for the purpose of measurement or the like, scaling-up is performed in a convolutional layer in a latter-half portion, and the "feature map" having the same size as the input image set can be obtained in the last convolutional layer. On the other hand, in the case of performing object detection, it is sufficient to output position information and thus scaling-up is not necessary.

The intermediate layer 562B may include a layer for performing batch normalization in addition to the convolutional layers 564 and the pooling layers 565. Batch normalization processing is the processing of normalizing a data distribution in units of mini batches for performing learning, and plays a role in quickly performing learning, reducing dependency on an initial value, suppressing overtraining, and so forth.

Processing in Output Layer

The output layer 562C is a layer that detects the position of a region of interest depicted in an input medical image (a normal-light image, a special-light image) on the basis of the feature quantity output from the intermediate layer 562B and outputs the result thereof. In the case of performing segmentation, the output layer 562C grasps the position of a region of interest depicted in an image in the pixel level by using the "feature map" acquired from the intermediate layer 562B. That is, the output layer 562C is capable of detecting, for each pixel of an endoscopic image, whether or not the pixel belongs to the region of interest, and outputting the detection result. On the other hand, in the case of performing object detection, determination in the pixel level is not necessary, and the output layer 562C outputs position information of a target.

The output layer 562C may execute discrimination (classification) of a lesion and output a discrimination result. For example, the output layer 562C may classify an endoscopic image into three categories "neoplastic", "non-neoplastic", and "others", and may output, as a discrimination result, three scores corresponding to "neoplastic", "non-neoplastic", and "others" (the sum of the three scores is 100%), or may output a classification result in a case where the endoscopic image can be clearly classified from the three scores. In the case of outputting a discrimination result, the output layer 562C may or may not include a fully connected layer as the last one or plural layers (see FIG. 4B).

The output layer 562C may output a measurement result of a region of interest. In the case of performing measurement by using the CNN, for example, the region of interest as a target may be segmented in the above-described manner and then measurement can be performed by the image processing unit 204 or the like on the basis of the result thereof. Alternatively, a measurement value of the region of interest as a target can be output directly from the recognizing unit 222. In the case where the measurement value is directly output, the image is caused to learn the measurement value, and thus regression of the measurement value occurs.

In the case of using the CNN having the above-described configuration, it is preferable to perform, in a learning procedure, a process of comparing a result output from the output layer 562C with a correct answer of recognition for the image set to calculate loss (error), and updating the weight parameters in the intermediate layer 562B from the layer on the output side toward the layer on the input side so that the loss is reduced (backpropagation).

Recognition Using Method Other than CNN

The recognizing unit 222 may perform recognition (detection or the like of a region of interest) by using a method other than the CNN. For example, a region of interest can be detected on the basis of a feature quantity of pixels of an acquired medical image. In this case, the recognizing unit 222 divides a detection target image into, for example, a plurality of rectangular regions, sets the rectangular regions obtained through the division as local regions, calculates, for each local region in the detection target image, a feature quantity (for example, hue) of pixels in the local region, and determines a local region having a specific hue among the local regions as a region of interest. Similarly, the recognizing unit 222 may perform classification or measurement based on a feature quantity.

Information Recorded in Recording Unit

Figure 6:
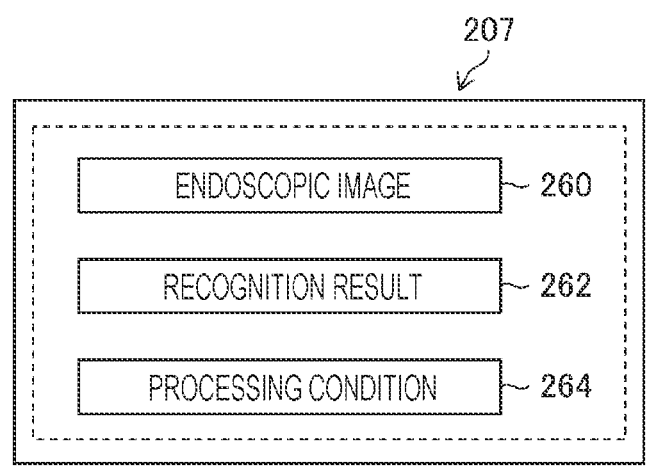
FIG. 6 is a diagram illustrating information recorded in a recording unit.

FIG. 6 is a diagram illustrating an example of information recorded in the recording unit 207. In the example in FIG. 6, an endoscopic image 260 (a medical image), a recognition result 262 (a result of recognition: detection, classification, measurement, etc.), and a processing condition 264 (a condition, a style, and the like of reporting or notification: see, for example, FIGS. 8 to 10) are recorded in association with each other under control by the recording control unit 230. The recording control unit 230 may record other information together.

Medical Image Processing Method

Figure 7:
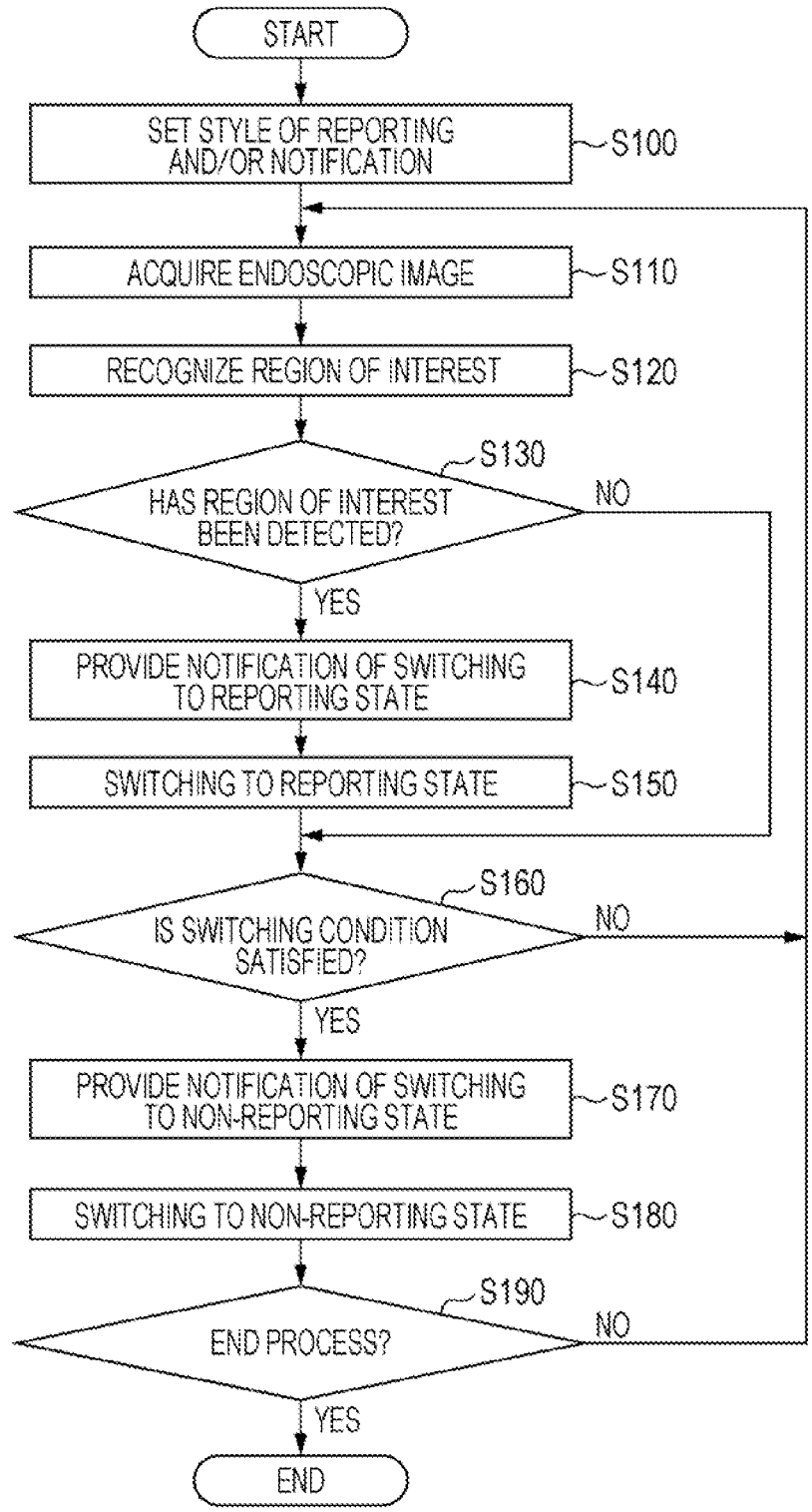
FIG. 7 is a flowchart illustrating a procedure of a medical image processing method according to the first embodiment.

A medical image processing method for the endoscope system 10 having the above-described configuration will be described with reference to the flowchart in FIG. 7. In the present embodiment, a description will be given mainly of a case where "recognition of a region of interest" is "detection of a region of interest". However, similar processing can be performed also in the case of "discrimination (classification) of a region of interest" or "measurement of a region of interest".

Setting about Reporting and Notification

The setting unit 228 sets a condition and/or a style of reporting and/or notification (switching notification) (step S100: setting step). The setting unit 228 is capable of making this setting in accordance with a user operation performed via the operation unit 208 and the monitor 400, as will be described below, for example.

Setting of Reporting Style

Figure 8:
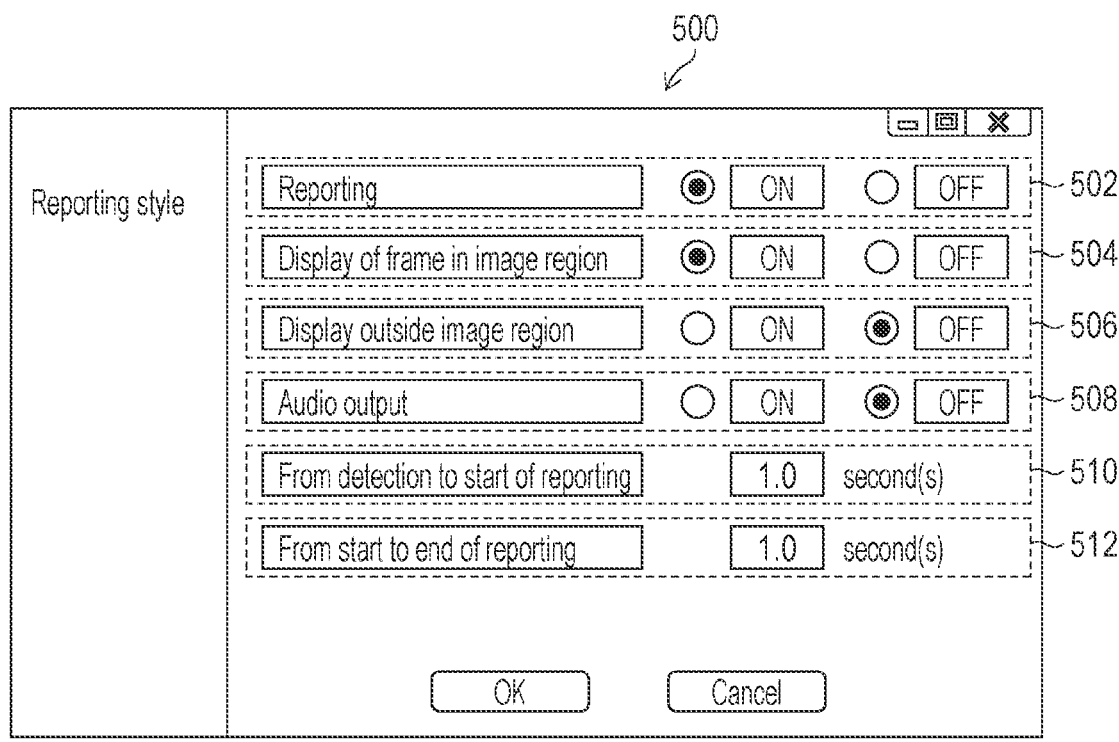
FIG. 8 is a diagram illustrating an example of a setting screen for a reporting style.

FIG. 8 is a diagram illustrating an example of a setting screen for a reporting style, and illustrates a state in which the setting unit 228 has displayed a screen 500 on the monitor 400 (broken lines in the figure are virtual lines indicating regions in the screen). The screen 500 has regions 502 to 508 in each of which radio buttons are disposed, and regions 510 to 512 in each of which a numerical value input field is disposed. A user is capable of setting whether reporting is to be performed (ON or OFF; region 502) by operating a radio button. Also, the user is capable of setting "whether reporting by display of a frame in an image region (for example, a frame 604 in FIG. 11B, 12B, or 12D) is to be performed" (region 504), "whether reporting by display of a frame outside an image region (for example, a frame 606 in FIG. 12C) is to be performed" (region 506), and "whether reporting by audio output (an audio signal) is to be performed" (region 508) by operating a radio button.

Furthermore, the user is capable of setting "an elapsed time ("determined time") from when a region of interest is detected to when reporting is started (to when switching from a non-reporting state to a reporting state occurs)" (region 510) and "an elapsed time ("determined time") from the start to end of reporting (to when switching from the reporting state to the non-reporting state occurs)" (region 512) by inputting a numerical value. The reporting unit 224 is switched from the reporting state to the non-reporting state after a time (seconds) input to the region 512 has elapsed. For inputting a numerical value, a method of selecting a determined numerical value from a pull-down menu may be used. In the example in FIG. 8, reporting is "ON", display of a frame is "ON", the time from detection to start of reporting is 1.0 second, and the time from the start to end of reporting is 1.0 second. With such switching to the non-reporting state, assistance can be finished and excessive assistance can be suppressed in accordance with needs of the user (in accordance with a predetermined condition).

The above-described example is an example of setting a style, and another item (reporting by light or vibration) may be set. In addition, the setting unit 228 may change settable items in accordance with the details of "recognition" (detection, discrimination, or measurement). For example, in the case of performing discrimination, the setting unit 228 is capable of setting ON/OFF of reporting and a reporting style regarding the type of a lesion, the range of a lesion, the size of a lesion, the macroscopic shape of a lesion, diagnosis of the stage of cancer, the present position in a lumen, the reliability of a discrimination result (computable with CNN), or the like.

Specific styles of reporting are illustrated in FIGS. 12A to 12D, which will be described below. A region for displaying a reporting style may be provided on the screen of the monitor 400 in accordance with a user operation (see a reporting style display region 610 in FIG. 12D).

In this way, in the endoscope system 10 (a medical image processing apparatus, an endoscope system), a user is capable of setting a reporting style as appropriate and the reporting unit 224 ends assistance (reporting) in accordance with a set condition, and thus excessive reporting can be suppressed. The setting of the style may be performed at any timing during processing, as well as at the start of medical image processing.

Setting of Notification Style

Notification of Switching from Reporting State to Non-Reporting State

Figure 9:
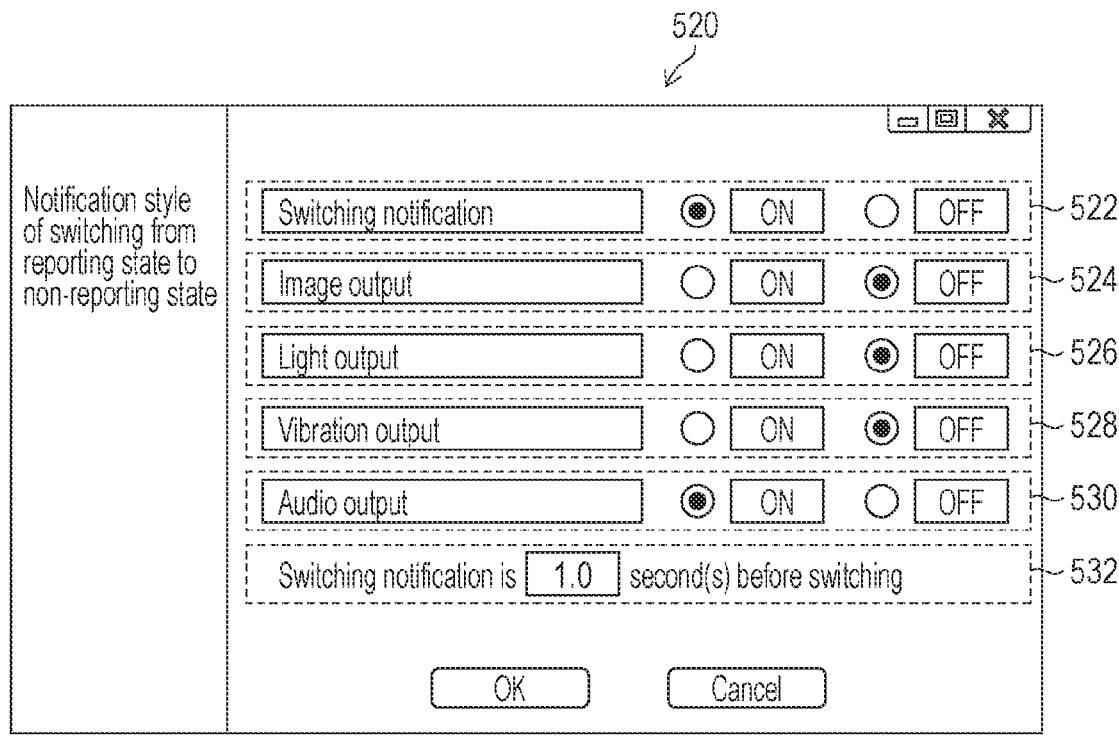
FIG. 9 is a diagram illustrating an example of a setting screen for a notification style.

FIG. 9 is a diagram illustrating an example of a setting screen for a notification style of switching from the reporting state to the non-reporting state (first style), and illustrates a state in which the setting unit 228 has displayed a screen 520 on the monitor 400. The screen 520 has regions 522 to 530 in each of which radio buttons are disposed, and a region 532 in which a numerical value input field is disposed. A user is capable of setting whether notification of switching from the reporting state to the non-reporting state is to be performed (ON or OFF; region 522) by operating a radio button. Also, the user is capable of setting whether switching notification by an image signal, a light signal, a vibration signal, or an audio signal is to be performed (regions 524 to 530) by operating a radio button. The switching notifying unit 226 is capable of performing notification by at least one of outputting an image to a display apparatus such as the monitor 400, blinking the light 214A, vibrating the vibrator 213A, or outputting audio from the speaker 209A, in accordance with the setting of a radio button.

Furthermore, the user is capable of setting "how many seconds before switching of the reporting state the switching notification is to be performed" by inputting a numerical value (region 532). In the example in FIG. 9, the switching notifying unit 226 performs notification one second (an example of a "determined time") before switching of the reporting state. If the user sets zero seconds, the switching notifying unit 226 performs notification at the same time as switching of the reporting state (step S170 described below: switching notification step). FIG. 9 is a diagram illustrating an example of a setting screen, and the setting unit 228 may accept a setting of a more detailed style (a specific pattern or the like of vibration, audio, blink, or display). In addition, the setting unit 228 may provide a region for displaying a switching notification style on the screen of the monitor 400 in accordance with a user operation (see a notification style display region 620 in FIGS. 11A and 11B).

In the endoscope system 10 (a medical image processing apparatus, an endoscope system), such settings make it possible to cause the user to sufficiently recognize an operation state of the assistance function (switching from the reporting state to the non-reporting state) while suppressing excessive assistance.

Notification of Switching from Non-Reporting State to Reporting State

Figure 10:
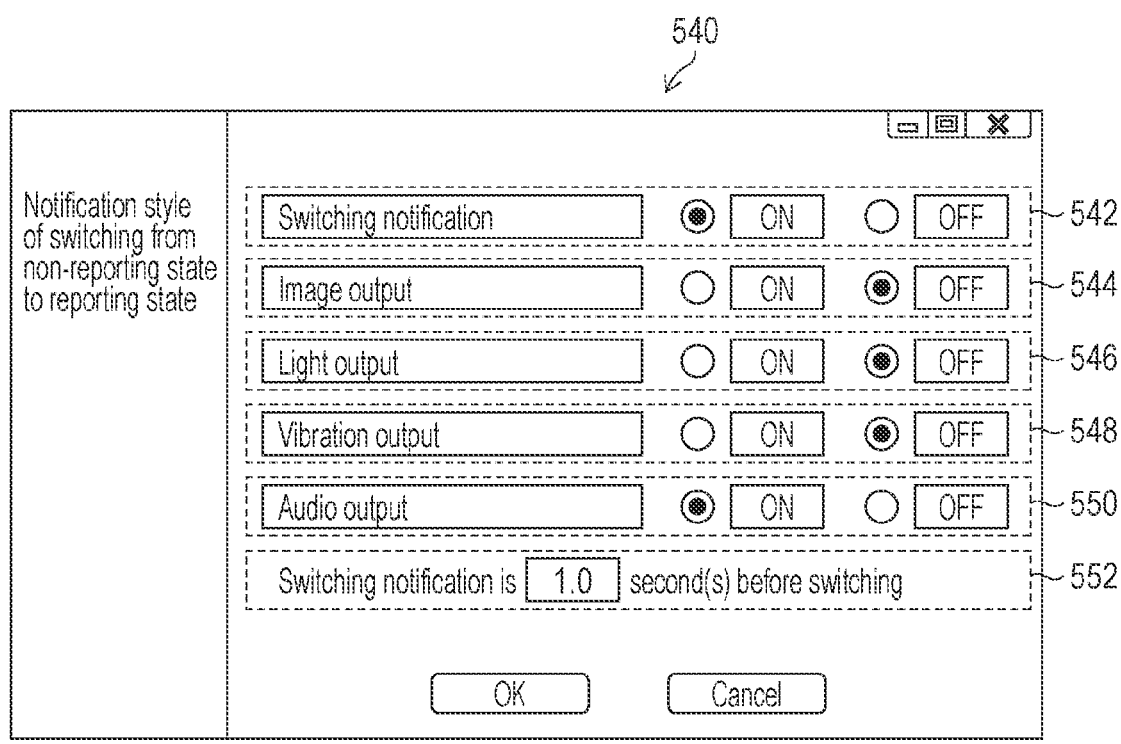
FIG. 10 is another diagram illustrating an example of a setting screen for a notification style.

FIG. 10 is a diagram illustrating an example of a setting screen for a notification style of switching from the non-reporting state to the reporting state (second style), and illustrates a state in which the setting unit 228 has displayed a screen 540 on the monitor 400. The screen 540 has regions 542 to 550 in each of which radio buttons are disposed, and a region 552 in which a numerical value input field is disposed. A user is capable of setting whether notification of switching from the non-reporting state to the reporting state is to be performed (ON or OFF; region 542) by operating a radio button. Also, the user is capable of setting whether notification by an image signal, a light signal, a vibration signal, or an audio signal is to be performed (regions 544 to 550) by operating a radio button. The switching notifying unit 226 is capable of performing notification by at least one of outputting an image to a display apparatus such as the monitor 400, blinking the light 214A, vibrating the vibrator 213A, or outputting audio from the speaker 209A, in accordance with the setting of a radio button. Furthermore, the user is capable of setting "how many seconds before switching of the reporting state the switching notification is to be performed" by inputting a numerical value (region 552).

In the example in FIG. 10, the switching notifying unit 226 performs notification one second (an example of a "determined time") before switching of the reporting state. If the user sets zero seconds, the switching notifying unit 226 performs notification at the same time as switching of the reporting state (step S140 described below: switching notification step). The setting unit 228 may provide a region for displaying a switching notification style on the screen of the monitor 400 in accordance with a user operation (see the notification style display region 620 in FIGS. 11A and 11B).

In the endoscope system 10 (a medical image processing apparatus, an endoscope system), such settings make it possible to cause the user to sufficiently recognize an operation state of the assistance function (switching from the non-reporting state to the reporting state) while suppressing excessive assistance.

The setting unit 228 may change the notification style of switching from the reporting state to the non-reporting state (first style) and the notification style of switching from the non-reporting state to the reporting state (second style) in accordance with a setting operation by a user. Changing of the style enables the user to clearly grasp the switching of the reporting state. The switching notifying unit 226 may perform "notification" of providing a notification of switching of the reporting state in a style different from a style of "reporting" of reporting that the recognizing unit has recognized a region of interest. The switching notifying unit 226 may give a warning to the user if the same styles are set. As a result of performing "notification" and "reporting" in different styles, the user is able to easily grasp which of "reporting" and "notification" is being performed. The "different styles" include a case where the type of a signal used for notification differs, such as audio and vibration or an image and light, and a case where the type of a signal is the same but the output pattern differs.

Acquisition of Endoscopic Image

The image acquiring unit 220 acquires a chronological endoscopic image (medical image) (step S110: image acquisition step). The image acquiring unit 220 may acquire an endoscopic image captured by the endoscope 100 or may acquire the endoscopic image 260 recorded in the recording unit 207. In a case where the image acquiring unit 220 acquires an endoscopic image captured by the endoscope 100, the recording control unit 230 is capable of recording the acquired image as the endoscopic image 260 in the recording unit 207.

Recognition of Region of Interest

The recognizing unit 222 (a recognizing unit: a detector, a classifier, a measurer) recognizes a region of interest in the endoscopic image acquired in step S110 (step S120: recognition step). The recognizing unit 222 is capable of performing, as "recognition", one or more of detection, classification, and measurement by using the above-described CNN or the like. For example, in a case where the "recognition" is "detection" of a region of interest, examples of the region of interest (region of concern) to be detected may include a polyp, a cancer, a colon diverticulum, an inflammation, a treatment scar (a scar of endoscopic mucosal resection (EMR), a scar of endoscopic submucosal dissection (ESD), a clip portion, or the like), a bleeding point, a perforation, angiodysplasia, and the like. Examples of "discrimination" of a region of interest may be determination of the type of a lesion (hyperplastic polyp, adenoma, intramucosal cancer, invasive cancer, or the like), the range of a lesion, the size of a lesion, the macroscopic shape of a lesion, diagnosis of the stage of cancer, a current position in a lumen (a pharynx, an esophagus, a stomach, a duodenum, or the like in an upper portion; a cecum, an ascending colon, a transverse colon, a descending colon, a sigmoid colon, a rectum, or the like in a lower portion), and the like.

A description will be given below of a case where a region of interest has not been detected and the reporting unit 224 is in the non-reporting state in an initial state (at the start of processing).

Switching from Non-Reporting State to Reporting State, and Switching Notification If the recognizing unit 222 has detected a region of interest (YES in step S130), the switching notifying unit 226 provides a notification indicating that the state of reporting will change from the non-reporting state to the reporting state (step S140: switching notification step). When the reporting is ON (see the region 502 in FIG. 8) after switching from the non-reporting state to the reporting state has been performed, the reporting unit 224 reports a recognition result in at least one style (for example, the frame 604 in FIG. 12B or 12D or the frame 606 in FIG. 12C) (step S150: reporting step). The reporting and notification may be performed in the styles set in step S100 (the style of notification is the second style), and there may be a time lag between detection of the region of interest and start of reporting (see the region 510 in FIG. 8). In addition, notification of switching (step S140) and switching of the reporting state (step S150) may be performed simultaneously or with a time lag (see the region 552 in FIG. 10).

Specific examples of notification and reporting in steps S140 and S150 are similar to those in FIGS. 11A to 12D described below (switching from the reporting state to the non-reporting state, and switching notification at that time).

Determination of Switching Condition

The reporting unit 224 determines whether a switching condition (a predetermined condition) is satisfied (step S160: determination step). The "switching condition" is a condition of switching from the reporting state to the non-reporting state, and the setting of time in the region 512 in FIG. 8 (the time from the start to end of reporting; 1.0 second in the example in the figure) or "a fact that a region of interest is not detected any more" can be used, for example.

Switching from Reporting State to Non-Reporting State, and Switching Notification If the determination in step S160 is affirmative, that is, "if the predetermined condition is satisfied after the start of the reporting state of performing reporting", the switching notifying unit 226 provides a notification indicating that switching from the reporting state to the non-reporting state is to occur (step S170: switching notification step), and the reporting unit 224 is switched to the non-reporting state of not performing reporting (step S180: reporting step). The time lag between switching and notification is set in accordance with the value input to the region 532 in FIG. 9. Notification may be performed before switching, or notification and switching may be simultaneously performed. The switching notifying unit 226 performs notification in the style set in FIG. 9 (a combination of signals to be output, a time lag).

Figure 11A:
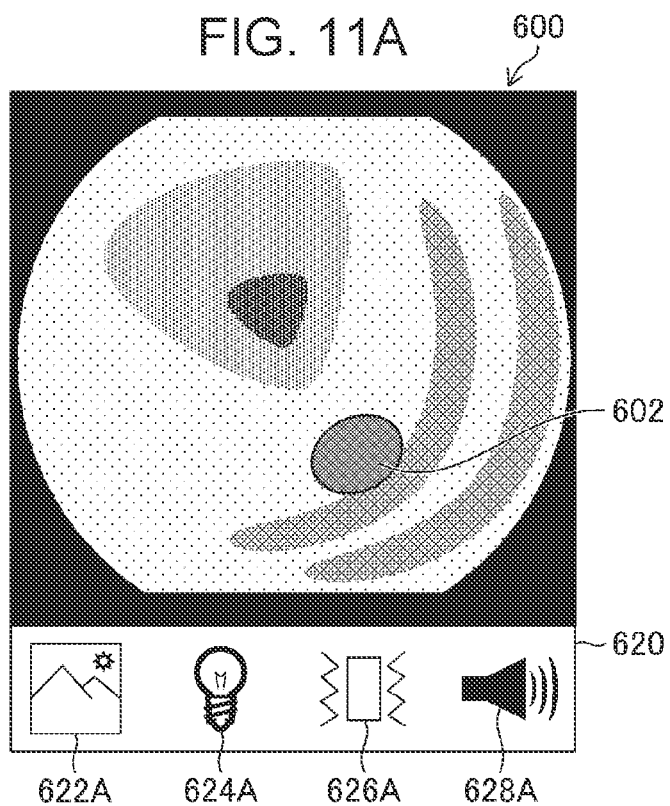
FIGS. 11A and 11B are diagrams illustrating examples of switching notification.
Figure 11B:
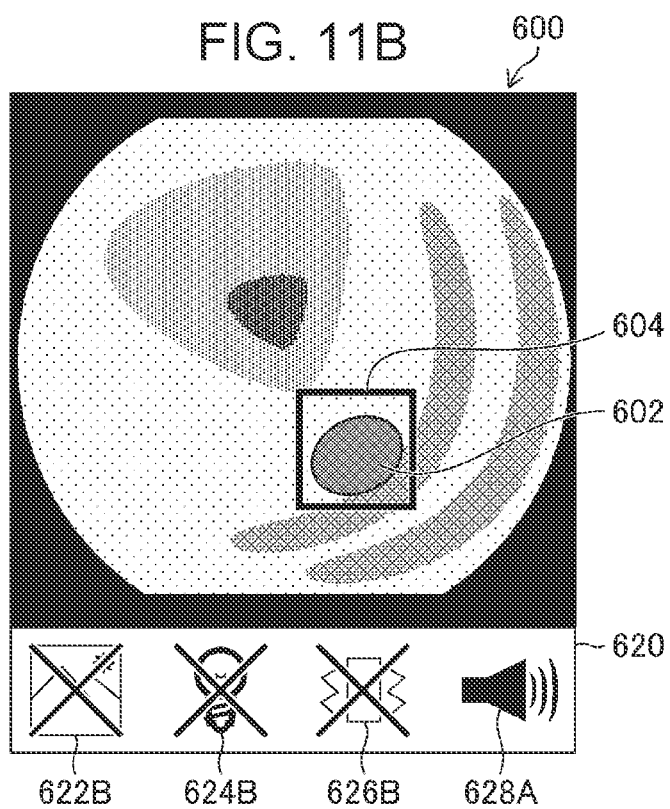

FIGS. 11A and 11B are diagrams illustrating examples of a notification style. FIG. 11A illustrates a state in which a region of interest 602 is seen in an image display region 600 on the monitor 400, and icons 622A to 628A representing an ON or OFF state of notification by an image signal, a light signal, a vibration signal, and an audio signal, respectively, are displayed in the notification style display region 620 outside the image display region 600. FIG. 11A illustrates a state in which all the icons 622A to 628A are in an ON state (notification by an image, light, vibration, and audio is to be performed), whereas FIG. 11B illustrates a state in which only the icon 628A representing notification by an audio signal is in an ON state and the others are in an OFF state (a cross is attached to each of the icons 622B to 626B). In FIG. 11B, the frame 604 (a style of reporting) surrounding a region of interest is displayed. The switching notifying unit 226 may turn ON or OFF the display of the notification style display region 620 in accordance with a user operation or in accordance with elapse of a determined time. In addition, the switching notifying unit 226 may provide a similar region for notification of switching from the non-reporting state to the reporting state.

Figure 12A:
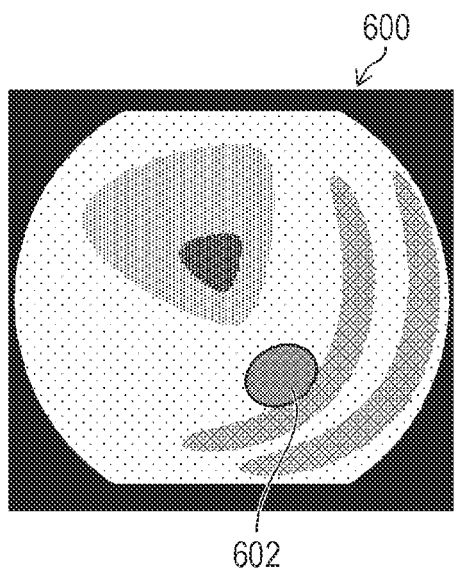
FIGS. 12A to 12D are diagrams illustrating states of reporting of a recognition result.
Figure 12B:
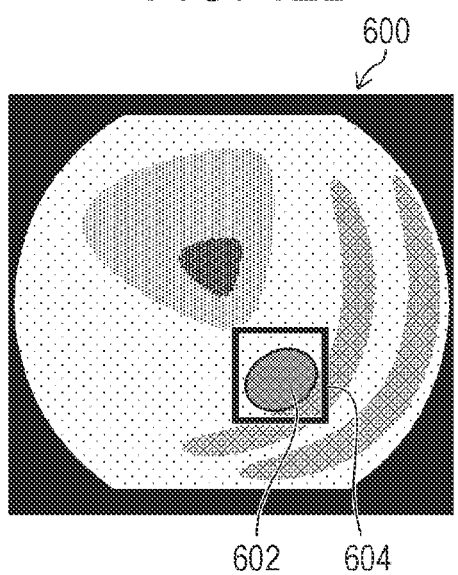
Figure 12C:
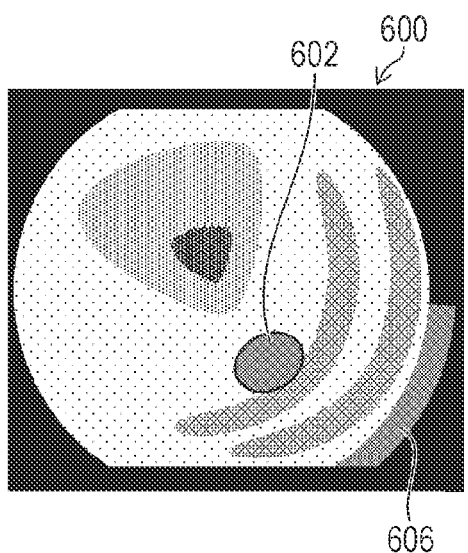
Figure 12D:
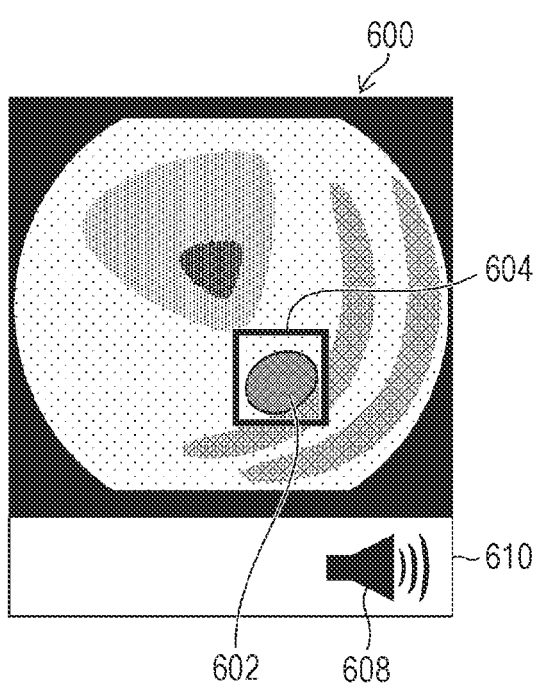

FIGS. 12A to 12D are diagrams illustrating examples of a reporting style. FIG. 12A illustrates, for comparison with FIGS. 12B to 12D, a state in which the region of interest 602 is seen in the image display region 600 on the monitor 400 but is not reported (for example, a state in which a set time has not elapsed). FIG. 12B illustrates a state in which the frame 604 surrounding the region of interest 602 is displayed (a case where the radio button is ON in the region 504 in FIG. 8). FIG. 12C illustrates a state in which the frame 606 is displayed outside the image display region 600 (a case where the radio button is ON in the region 506 in FIG. 8). FIG. 12D illustrates a state in which the frame 604 and audio are output (a case where the radio box in ON in the regions 504 and 508 in FIG. 8).

The reporting unit 224 is capable of displaying an icon representing an ON/OFF state of an output signal similarly to the case of notification (see FIGS. 11A and 11B). Specifically, as in FIG. 12D, for example, the reporting unit 224 is capable of displaying, in the reporting style display region 610, an icon 608 representing ON/OFF of output of an audio signal. The reporting unit 224 may turn OFF the display of the reporting style display region 610 in accordance with a user operation or after a certain time has elapsed since the start of the display. Such turning OFF of display makes it possible to suppress excessive reporting.

Timing at which Switching Notification can be Performed

Figure 13A:
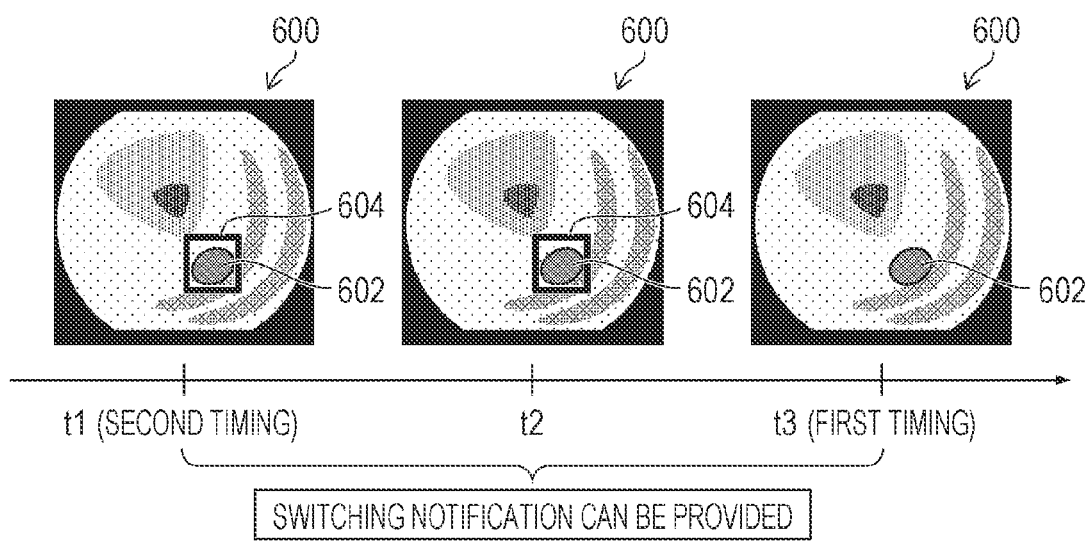
FIGS. 13A and 13B are diagrams illustrating timings at which a switching notification can be provided.
Figure 13B:
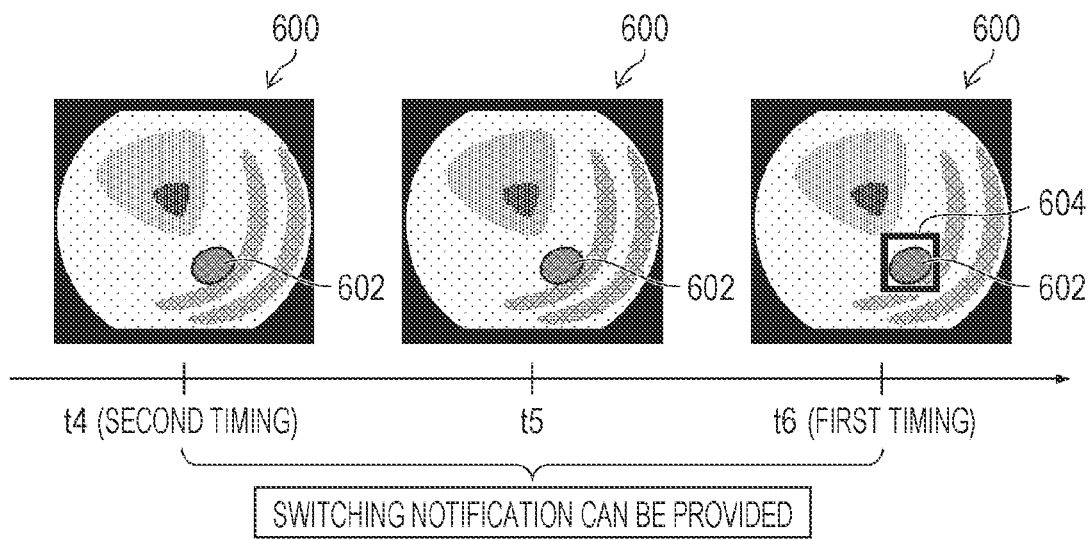

FIGS. 13A and 13B are diagrams illustrating timings at which switching notification can be performed. FIG. 13A illustrates a state of switching from the reporting state to the non-reporting state, and illustrates that the frame 604 surrounding the region of interest 602 is hidden after a determined time has elapsed (see the region 512 in FIG. 8). As illustrated in the figure, the switching notifying unit 226 is capable of performing switching notification at any timing (including a time point t2 that is a middle point between time points t1 and t3) between the time point t3 at which switching from the reporting state to the non-reporting state is performed (a "first timing" at which at least one reporting style is switched) and the time point t1 (a second timing) that is a determined time before the time point t3. If notification is performed at the time point t3, the notification and the end of reporting (switching to the non-reporting state) are performed simultaneously. As described above, the user is capable of inputting the time lag (how many seconds before the time point t3 the notification is to be performed) in the region 532 in FIG. 9.

FIG. 13B illustrates a state of switching from the non-reporting state to the reporting state, and illustrates that the frame 604 surrounding the region of interest 602 is displayed after a determined time has elapsed since detection (see the region 510 in FIG. 8). As illustrated in the figure, the switching notifying unit 226 is capable of performing switching notification at any timing (including a time point t5 that is a middle point between time points t4 and t6) between the time point t6 at which switching from the non-reporting state to the reporting state is performed (the above-described "first timing") and the time point t4 (the second timing) that is a determined time before the time point t6. If notification is performed at the time point t6, the notification and the start of reporting (switching to the reporting state) are performed simultaneously. As described above, the user is capable of inputting the time lag (how many seconds before the time point t6 the notification is to be performed) in the region 552 in FIG. 10.

End of Process

The image processing unit 204 repeats the process of step S110 to step S180 until the process ends (until "YES" is obtained in step S190). The image processing unit 204 is capable of ending the process in accordance with, for example, a user operation performed on the handheld operation section 102 or the operation unit 208.

Advantages of Embodiment

As described above, the endoscope system 10 according to the present embodiment is capable of performing assistance in a desired style in accordance with needs of a user while suppressing excessive assistance. In addition, the endoscope system 10 is capable of causing the user to sufficiently recognize an operation state of an assistance function (switching from the reporting state to the non-reporting state, and switching from the non-reporting state to the reporting state).

Recognition of Region of Interest Using Method Other Than Image Processing

In the embodiment described above, a description has been given of the case of recognizing a region of interest by using image processing on a medical image, but the recognizing unit 222 may recognize a region of interest without using image processing on a medical image (step S120: recognition step). The recognizing unit 222 is capable of recognizing (detecting, discriminating (classifying), measuring) a region of interest by using, for example, audio input, image recognition of a gesture, or an operation of a device such as a foot switch, of a user. In addition, in the medical image processing apparatus, the endoscope system, and the medical image processing method according to the present invention, reporting and notification are performed similarly to the above-described embodiment also in the case of performing recognition without using processing on a medical image, and this enables a user to sufficiently recognize an operation state of an assistance function.

Application to Images Other Than Endoscopic Image

In the above-described embodiment, a description has been given of the case of performing recognition by using an endoscopic image, which is an aspect of a medical image. The medical image processing apparatus and the medical image processing method according to the present invention can also be applied to the case of using a medical image other than an endoscopic image, such as an ultrasound image.

Appendices

In addition to the above-described embodiment, the configurations described below are included in the scope of the present invention.

Appendix 1

A medical image processing apparatus wherein
a medical image analysis processing unit detects a region of interest on the basis of a feature quantity of pixels of a medical image, the region of interest being a region to be focused on, and
a medical image analysis result acquiring unit acquires an analysis result of the medical image analysis processing unit.

Appendix 2

A medical image processing apparatus wherein
a medical image analysis processing unit detects presence or absence of a target to be focused on the basis of a feature quantity of pixels of a medical image, and
a medical image analysis result acquiring unit acquires an analysis result of the medical image analysis processing unit.

Appendix 3

The medical image processing apparatus wherein
the medical image analysis result acquiring unit acquires the analysis result of the medical image from a recording device in which the analysis result is recorded, and
the analysis result is either or both of the region of interest which is a region to be focused on included in the medical image and the presence or absence of the target to be focused on.

Appendix 4

The medical image processing apparatus wherein the medical image is a normal-light image acquired by radiating light in a white range or light in a plurality of wavelength ranges as the light in the white range.

Appendix 5

The medical image processing apparatus wherein
the medical image is an image acquired by radiating light in a specific wavelength range, and
the specific wavelength range is a range narrower than a white wavelength range.

Appendix 6

The medical image processing apparatus wherein the specific wavelength range is a blue or green range in a visible range.

Appendix 7

The medical image processing apparatus wherein the specific wavelength range includes a wavelength range of 390 nm or more and 450 nm or less or a wavelength range of 530 nm or more and 550 nm or less, and the light in the specific wavelength range has a peak wavelength in the wavelength range of 390 nm or more and 450 nm or less or the wavelength range of 530 nm or more and 550 nm or less.

Appendix 8

The medical image processing apparatus wherein the specific wavelength range is a red range in a visible range.

Appendix 9

The medical image processing apparatus wherein the specific wavelength range includes a wavelength range of 585 nm or more and 615 nm or less or a wavelength range of 610 nm or more and 730 nm or less, and the light in the specific wavelength range has a peak wavelength in the wavelength range of 585 nm or more and 615 nm or less or the wavelength range of 610 nm or more and 730 nm or less.

Appendix 10

The medical image processing apparatus wherein the specific wavelength range includes a wavelength range in which a light absorption coefficient is different between oxyhemoglobin and deoxyhemoglobin, and the light in the specific wavelength range has a peak wavelength in the wavelength range in which the light absorption coefficient is different between oxyhemoglobin and deoxyhemoglobin.

Appendix 11

The medical image processing apparatus wherein the specific wavelength range includes a wavelength range of 400±10 nm, a wavelength range of 440±10 nm, a wavelength range of 470±10 nm, or a wavelength range of 600 nm or more and 750 nm or less, and the light in the specific wavelength range has a peak wavelength in the wavelength range of 400±10 nm, the wavelength range of 440±10 nm, the wavelength range of 470±10 nm, or the wavelength range of 600 nm or more and 750 nm or less.

Appendix 12

The medical image processing apparatus wherein
the medical image is an inside-of-living-body image depicting an inside of a living body, and
the inside-of-living-body image has information about fluorescence emitted by a fluorescent substance in the living body.

Appendix 13

The medical image processing apparatus wherein the fluorescence is acquired by irradiating the inside of the living body with excitation light whose peak is 390 nm or more and 470 nm or less.

Appendix 14

The medical image processing apparatus wherein
the medical image is an inside-of-living-body image depicting an inside of a living body, and
the specific wavelength range is a wavelength range of infrared light.

Appendix 15

The medical image processing apparatus wherein the specific wavelength range includes a wavelength range of 790 nm or more and 820 nm or less or a wavelength range of 905 nm or more and 970 nm or less, and the light in the specific wavelength range has a peak wavelength in the wavelength range of 790 nm or more and 820 nm or less or the wavelength range of 905 nm or more and 970 nm or less.

Appendix 16

The medical image processing apparatus wherein
a medical image acquiring unit includes a special-light image acquiring unit that acquires a special-light image having information about the specific wavelength range on the basis of a normal-light image that is acquired by radiating light in a white range or light in a plurality of wavelength ranges as the light in the white range, and
the medical image is the special-light image.

Appendix 17

The medical image processing apparatus wherein a signal in the specific wavelength range is acquired through computation based on color information of RGB or CMY included in the normal-light image.

Appendix 18

The medical image processing apparatus including
a feature quantity image generating unit that generates a feature quantity image through computation based on at least one of a normal-light image or a special-light image, the normal-light image being acquired by radiating light in a white range or light in a plurality of wavelength ranges as the light in the white range, the special-light image being acquired by radiating light in a specific wavelength range, wherein
the medical image is the feature quantity image.

Appendix 19

An endoscope apparatus including:
the medical image processing apparatus according to any one of appendices 1 to 18; and
an endoscope that acquires an image by radiating at least any one of light in a white wavelength range or light in a specific wavelength range.

Appendix 20

A diagnosis assistance apparatus including the medical image processing apparatus according to any one of appendices 1 to 18.

Appendix 21

A medical work assistance apparatus including the medical image processing apparatus according to any one of appendices 1 to 18.

The embodiment of the present invention and other examples have been described above. The present invention is not limited to the above-described aspects and various modifications can be made without deviating from the spirit of the present invention.

REFERENCE SIGNS LIST

10 endoscope system
100 endoscope
102 handheld operation section
104 insertion section
106 universal cable
108 light guide connector
112 soft part
114 bending part
116 tip rigid part
116A distal-end-side surface
123 illumination unit
123A illumination lens
123B illumination lens
126 forceps port
130 imaging optical system
132 imaging lens
134 imaging element
136 driving circuit
138 AFE
141 air/water supply button
142 suction button
143 function button
144 imaging button
170 light guide
200 processor
202 image input controller 204 image processing unit
205 communication control unit
206 video output unit
207 recording unit
208 operation unit
209 audio processing unit
209A speaker
210 CPU
211 ROM
212 RAM
213 vibration control unit
213A vibrator
214 blink control unit
214A light
220 image acquiring unit
222 recognizing unit
224 reporting unit
226 switching notifying unit
228 setting unit
230 recording control unit
260 endoscopic image
262 recognition result
264 processing condition
300 light source apparatus
310 light source
310B blue light source
310G green light source
310R red light source
310V violet light source
330 diaphragm
340 condenser lens
350 light source control unit
400 monitor
500 screen
502 region
504 region
506 region
508 region
510 region
512 region
520 screen
522 region
524 region
526 region
528 region
530 region
532 region
540 screen
542 region
544 region
546 region
548 region
550 region
552 region
562A input layer
562B intermediate layer
562C output layer
564 convolutional layer
565 pooling layer
566 fully connected layer
600 image display region
602 region of interest
604 frame
606 frame
608 icon
610 reporting style display region
620 notification style display region
622A icon
622B icon
624A icon
624B icon
626A icon
626B icon
628A icon
$F_1$ filter
$F_2$ filter
S100 to S190 individual steps of medical image processing method

What is claimed is:

1. A medical image processing apparatus comprising:
one or more processors configured to process:
acquiring that acquires a medical image;
recognizing that performs recognition of a region of interest in the acquired medical image;
reporting that performs reporting of position information of the region of interest as a result of the recognition in a first state which is capable of performing the reporting and is a state in response to satisfying a predetermined condition;
setting that sets determined time in response to user input;
switching that switches from the first state to a second state of not performing the reporting, in response to elapsing the determined time; and
notifying that provides a first notification indicating the switching from the first state to the second state in a first style.

2. The medical image processing apparatus according to claim 1, wherein the notifying includes providing a second notification indicating switching from the second state to the first state in a second style.

3. The medical image processing apparatus according to claim 2, wherein the first style is different from the second style.

4. The medical image processing apparatus according to claim 1, wherein the determined time is time from the recognizing the region of interest.

5. The medical image processing apparatus according to claim 1, wherein the first notification is configured to notify before the switching from the first state to the second state.

6. The medical image processing apparatus according to claim 1, wherein the first notification is configured to notify at the same time as the switching from the first state to the second state.

7. The medical image processing apparatus according to claim 1, wherein the first style uses at least one of an audio signal, a light signal, an image signal, or a vibration signal.

8. The medical image processing apparatus according to claim 1, wherein the first style is different from a style of the reporting.

9. The medical image processing apparatus according to claim 1, wherein the processor is further configured to process setting that sets a style of the reporting and/or the first notification.

10. The medical image processing apparatus according to claim 1, wherein the recognizing performs the recognition of the region of interest without image processing on the medical image.

11. The medical image processing apparatus according to claim 1, wherein:
the setting includes a reporting setting whether the reporting is to be performed; and
the predetermined condition is ON setting of the reporting setting.

12. The medical image processing apparatus according to claim 1, wherein:
the setting includes a start time setting in a case in which the reporting is started from the recognition of the region of interest; and
the predetermined condition is elapsing the start time.

13. The medical image processing apparatus according to claim 1, wherein the determined time is time from timing of switching from the second state to the first state.

14. The medical image processing apparatus according to claim 1, wherein the position information is a frame.

15. The medical image processing apparatus according to claim 1, wherein:
the acquiring acquires medical images including the medical image, the medical images being chronological images;
the recognizing performs the recognition for the respective medical images; and
the reporting performs the reporting of the position information for the respective medical images.

16. An endoscope system comprising:
the medical image processing apparatus according to claim 14;
a display apparatus that displays the medical image; and
an endoscope that is to be inserted into a subject and has an imaging unit that captures the medical image.

17. A medical image processing method comprising:
an image acquisition step of acquiring a medical image;
a recognition step of performing recognition of a region of interest in the acquired medical image;
a reporting step of reporting position information of the region of interest as a result of the recognition in a first state which is capable of performing the reporting and is a state in response to satisfying a predetermined condition;
a setting step that sets determined time in response to user input;
a switching step of switching from the first state to a second state of not performing the reporting, in response to elapsing the determined time; and
a notification step of providing a notification indicating the switching from the first state to the second state in a first style.

18. The medical image processing method according to claim 17, wherein:
the setting step includes a reporting setting whether the reporting is to be performed; and
the predetermined condition is ON setting of the reporting setting.

19. The medical image processing method according to claim 17, wherein:
the setting step includes a start time setting in a case in which the reporting is started from the recognition of the region of interest; and
the predetermined condition is elapsing the start time.

20. The medical image processing method according to claim 17, wherein the determined time is time from timing of switching from the second state to the first state.

21. The medical image processing method according to claim 17, wherein the notification step notifies the notification before the switching from the first state to the second state.

22. The medical image processing method according to claim 17, wherein the notification step notifies the notification at the same time as the switching from the first state to the second state.

23. The medical image processing method according to claim 17 wherein:
the image acquisition step acquires medical images including the medical image, the medical images being chronological images;
the recognition step performs the recognition for the medical images; and
the reporting step performs the reporting of the position information for the respective medical images.

* * * * *